United States Patent [19]

Janssen et al.

[11] Patent Number: 4,607,045

[45] Date of Patent: Aug. 19, 1986

[54] AZOLYLMETHYLCYCLOACETALS, THEIR PREPARATION AND THEIR USE AS DRUGS

[75] Inventors: Bernd Janssen, Ludwigshafen; Friedrich-Wilhelm Kohlmann, Moorrege; Walter Wesenberg, Bujendorf ueber Eutin; Wolfgang Heberle, Stuttgart, all of Fed. Rep. of Germany

[73] Assignee: BASF Aktiengesellschaft, Ludwigshafen, Fed. Rep. of Germany

[21] Appl. No.: 691,851

[22] Filed: Jan. 16, 1985

[30] Foreign Application Priority Data

Jan. 19, 1984 [DE] Fed. Rep. of Germany ....... 3401694

[51] Int. Cl.$^4$ .................. A01N 43/50; A01N 43/653; C07D 405/06; A61K 31/41
[52] U.S. Cl. .................... 514/383; 260/349; 514/397; 548/262; 548/336; 549/373; 549/451
[58] Field of Search ............... 548/262, 336; 514/383, 514/397

[56] References Cited

U.S. PATENT DOCUMENTS 4,313,953 2/1982 Heeres et al. ............ 514/383
4,402,963 9/1983 Sturm ..................... 548/262

FOREIGN PATENT DOCUMENTS 0052905  6/1982  European Pat. Off. ........... 548/336
0094052 11/1983  European Pat. Off. ........... 548/262
0134089  8/1983  Japan ........................ 548/336
1244530  9/1971  United Kingdom .............. 548/341
2026486  2/1980  United Kingdom .............. 548/262
2027701  2/1980  United Kingdom .............. 548/262
1594859  8/1981  United Kingdom .............. 548/262

Primary Examiner—Alton D. Rollins
Attorney, Agent, or Firm—Keil & Weinkauf

[57] ABSTRACT

Azolylmethylcycloacetals of the formula I

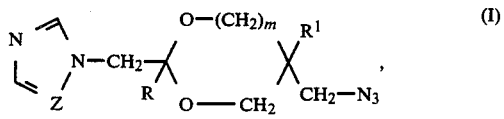

where R is phenyl which can be substituted by halogen, or is $C_1$–$C_6$-alkyl, $R^1$ is hydrogen or $C_1$–$C_3$-alkyl, Z is CH or N, and m is 0 or 1, and their physiologically tolerated addition salts with acids and their preparation are described.

The novel substances have an antimycotic action.

7 Claims, No Drawings

AZOLYLMETHYLCYCLOACETALS, THEIR PREPARATION AND THEIR USE AS DRUGS

The present invention relates to novel azolylmethylcycloacetals, processes for their preparation, therapeutic agents which contain these compounds and can be used as antimycotics, and their use in the treatment of disorders.

A large number of antimycotic active compounds, for example azolylmethylcarbinols, such as miconazole (German Laid-Open Application DOS No. 1,940,388), and azolylmethyldioxolanes, such as ketoconazole (German Laid-Open Application DOS No. 2,804,096) have been disclosed, but their actions are not always satisfactory (Zeitschrift für Hautkrankheiten 56 (1981), 1109). The compounds of the present invention differ from the compounds of the last-mentioned type essentially in the type of the substituents, especially in the 5- or 4-position of the dioxane or dioxolane framework, respectively.

We have found that azolylmethylcycloacetals of the formula I

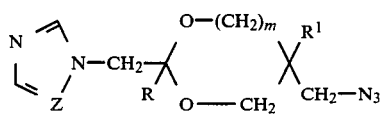

where R is phenyl which can be substituted by halogen, or is $C_1$-$C_6$-alkyl, $R^1$ is hydrogen or $C_1$-$C_3$-alkyl, Z is CH or N and m is 0 or 1, and their physiologically tolerated addition salts with acids possess good antimicrobial, in particular antimycotic, properties.

In formula I, R is preferably tert.-butyl, or is phenyl which is substituted by halogen, in particular by chlorine. Among the latter compounds, 2,4-dichlorophenyl is particularly suitable.

$R^1$ is preferably hydrogen or methyl.

The novel compounds of the formula I contain chiral centers and are obtained in general in the form of racemates or as diastereomer mixtures of erythro and threo forms. The erythro and threo diastereomers of the novel compounds can be separated, for example, by utilizing their different solubilities or by column chromatography and can be isolated in pure form. Such pure diastereomer pairs can be converted to pure enantiomers by a conventional method. The pure diastereomers and enantiomers as well as mixtures of these can be used as antimicrobial agents.

Preferred acids for forming physiologically tolerated salts are hydrohalic acids, such as hydrobromic acid and, in particular, hydrochloric acid, with which the novel compounds give particularly readily crystallizing salts. Other examples are phosphoric acid, nitric acid, sulfuric acid, monofunctional and bifunctional carboxylic acids and hydroxycarboxylic acids, such as acetic acid, oxalic acid, maleic acid, succinic acid, fumaric acid, tartaric acid, citric acid, salicylic acid, sorbic acid or lactic acid, and sulfonic acids, such as p-toluenesulfonic acid and naphthalene-1,5-disulfonic acid.

The novel azolylmethylcycloacetals of the formula I can be prepared by a method in which
(a) a cycloacetal of the formula II

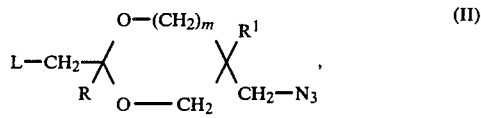

where R, $R^1$ and m have the above meanings and L is a leaving group which can undergo nucleophilic substitution, is reacted with a compound of the formula III

where Z has the above meanings, or
(b) a cycloacetal of the formula IV

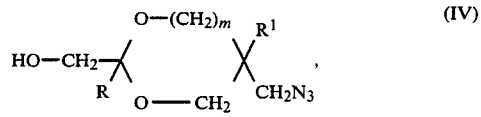

where R, $R^1$ and m have the above meanings, is reacted with a compound of the formula V

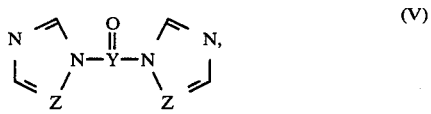

where Z has the above meanings and Y is a carbon or sulfur atom, or
(c) a compound of the formula VI

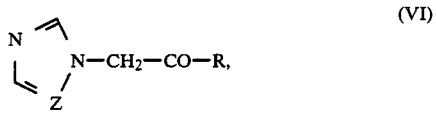

where Z and R have the above meanings, is reacted with a compound of the formula VII

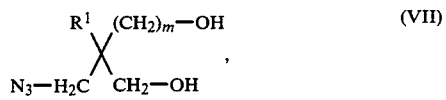

where $R^1$ and m have the above meanings, or
(d) a compound of the formula VIII

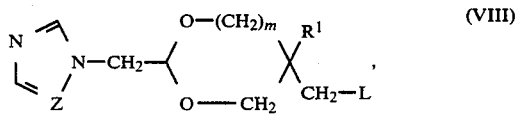

where Z, R, $R^1$ and m have the above meanings and L is a leaving group which can undergo nucleophilic substitution, is reacted with an alkali metal azide, and the resulting compound is, if required, converted to its physiologically tolerated addition salts with acids.

Among these processes, the last-mentioned one (d) is preferred.

Reaction (a) is preferably carried out in the presence of a solvent or diluent, with or without the addition of an inorganic or organic base and of a reaction accelerator, at from 10° to 120° C. The preferred solvents and diluents include ketones, such as acetone, methyl ethyl ketone or cyclohexanone, nitriles such as acetonitrile, esters, such as ethyl acetate, ethers, such as diethyl ether, tetrahydrofuran or dioxane, sulfoxides, such as dimethyl sulfoxide, amides, such as dimethylformamide, dimethylacetamide or N-methylpyrrolidone, and sulfolane, or mixtures of these.

Suitable bases, which, if necessary, can also be used in the reaction as acid acceptors, are alkali metal hydroxides, such as lithium hydroxide, sodium hydroxide or potassium hydroxide, alkali metal carbonates, such as sodium carbonate, potassium carbonate, sodium bicarbonate or potassium bicarbonate, pyridine, 4-dimethylaminopyridine and excess 1,2,4-triazole or imidazole. However, other conventional bases can also be used.

Preferred reaction accelerators are metal halides, such as sodium iodide or potassium iodide, quaternary ammonium salts, such as tetrabutylammonium chloride, bromide or iodide or benzyltriethylammonium chloride or bromide, and crown ethers, such as 12-crown-4, 15-crown-5, 18-crown-6, dibenzo-18-crown-6 or dicyclohexano-18-crown-6.

The reaction is carried out in general at from 10° to 120° C., under atmospheric or superatmospheric pressure, continuously or batchwise.

Reaction (a) can also be carried out as follows: compound III is converted to a metal salt, preferably an alkali metal salt, and this is reacted with compound II at from −10° to +120° C., in the presence or absence of a solvent or diluent and with or without the addition of a strong inorganic or organic base. The preferred solvents and diluents include amides, such as dimethylformamide, diethylformamide, dimethylacetamide, diethylacetamide, N-methylpyrrolidone, hexamethylphosphorotriamide and sulfoxides, such as dimethyl sulfoxide and sulfolane.

Examples of suitable bases, which can also be used in the reaction as acid acceptors, are alkali metal hydrides, such as lithium hydride, sodium hydride or potassium hydride, alkali metal amides, such as sodium amide or potassium amide, and sodium tert.-butoxide, potassium tert.-butoxide, lithium-triphenylmethyl, sodium-triphenylmethyl, potassium-triphenylmethyl, naphthalene-lithium, sodium and naphthalene-potassium.

L is preferably a halogen atom or a reactive ester group, e.g. the mesylate group.

Reaction (b) is carried out in a solvent or diluent, suitable solvents and diluents being polar organic solvents, such as nitriles, e.g. acetonitrile, sulfoxides, e.g. dimethyl sulfoxide, formamides, e.g. dimethylformamide, ketones, e.g. acetone, ethers, e.g. diethyl ether or tetrahydrofuran, and in particular chlorohydrocarbons, e.g. methylene chloride or chloroform.

The reaction is carried out in general at from 0° to 100° C., preferably at from 20° to 80° C. When a solvent is present, the procedure is advantageously effected at the boiling point of the particular solvent.

In carrying out process (b), about 1 mole of bis-1,2,4-triazol-1-yl ketone or bis-imidazol-1-yl ketone, or preferably about 1 mole of bis-1,2,4-triazol-1-yl sulfoxide or bis-imidazol-1-yl sulfoxide, is employed per mole of the compound of the formula IV, or bis-1,2,4-triazol-1-yl sulfoxide or bis-imidazol-1-yl sulfoxide is produced in situ.

Reaction (c) is preferably carried out by refluxing the two reactants in a suitable organic solvent, preferably in the presence of a simple alcohol, such as ethanol, propanol, butanol or pentanol, and in the presence of a suitable strong acid, such as 4-methylbenzenesulfonic acid, with azeotropic removal of water. Examples of suitable organic solvents are aromatic hydrocarbons, such as benzene, methylbenzene or dimethylbenzene, saturated hydrocarbons, such as cyclohexane, and mixtures of these.

Reaction (d) is preferably carried out in the presence of a solvent or diluent, with or without the addition of an inorganic or organic base and of a reaction accelerator, at from 10° to 120° C. The preferred solvents and diluents include ketones, such as acetone, methyl ethyl ketone or cyclohexanone, nitriles, such as acetonitrile, esters, such as ethyl acetate, ethers, such as diethyl ether, tetrahydrofuran or dioxane, sulfoxides, such as dimethyl sulfoxide, amides, such as dimethylformamide, dimethylacetamide or N-methylpyrrolidone, and sulfolane and mixtures of these.

Examples of suitable bases, which can, if necessary, also be used in the reaction as acid acceptors, are alkali metal hydroxides, such as lithium hydroxide, sodium hydroxide or potassium hydroxide, alkali metal carbonates, such as sodium carbonate, potassium carbonate, sodium bicarbonate or potassium bicarbonate, pyridine, 4-dimethylaminopyridine and an excess of alkali metal azide.

Suitable reaction accelerators are the substances stated for process (a).

The reaction is carried out in general at from 10° to 120° C., under atmospheric or superatmospheric pressure, continuously or batchwise.

The resulting compounds of the formula I are isolated by a conventional method and, if required, are converted to their salts with the stated acids.

The starting compounds II are obtainable by the following route:

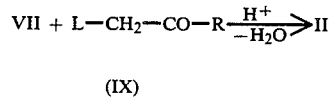

(IX)

For this purpose, the reactants are reacted by process (b) described above, with azeotropic removal of water.

The starting compounds of the formula VI are known; those which are unknown can be prepared in a conventional manner, for example as described in German Patent No. 2,549,798 or German Laid-Open Application DOS No. 2,940,133.

The starting compounds VII are obtainable in accordance with the following equation:

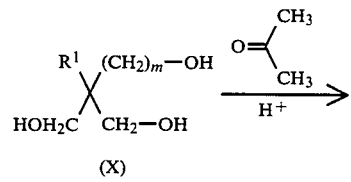

(X)

-continued

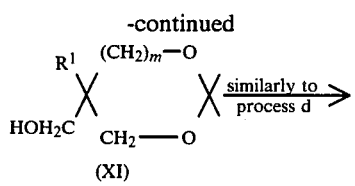

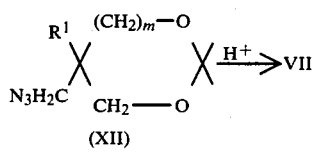

Some of the starting compounds of the formula VIII are known from the literature (J. Med. Chem. 12 (1969), 788 and 22 (1979) 1003, and U.S. Pat. Nos. 4,101,664, 4,101,665, 4,139,540 and 4,338,327); those which are unknown can be prepared in a similar manner.

Surprisingly, the novel azole derivatives, in addition to possessing very good in vitro antimycotic activity, also have a better therapeutically useful in vivo activity than conventional preparations, in particular against dermatophytes, but also against Candida. They also possess antibacterial activity. The active compounds according to the invention therefore constitute a valuable enrichment of the art.

The action against dermatophytes, bacteria and protozoa can be demonstrated by methods as described in, for example, P. Klein, Bakteriologische Grundlagen der chemotherapeutischen Laboratoriumspraxis, Springer-Verlag Berlin, 1957. The action against yeasts was demonstrated in the pseudomycelium and mycelium phase tests with Candida albicans (cf. German Laid-Open Application DOS No. 3,010,093).

The minimum inhibitory concentrations (MIC) achieved in the agar dilution test were determined.

The results are summarized in Table 1.

TABLE 1

| | In vitro antimicrobial activity of the novel compounds | | | | | | | | |
|---|---|---|---|---|---|---|---|---|---|
| Substance of Example No. | Epid. flocc. | Microsp. ferrug. | Trichoph. ment. | Cand. alb. yeast phase | Cand. alb. mycelium phase | Abs. corym. | Asp. fum. | Mucor pus | Staph. aur. |
| 1 | 0.25 | 0.125 | 1 | >16 | 0.0625 | >16 | 4 | 8 | 128 |
| 2 | 0.0156 | 0.0156 | 0.0312 | >16 | 0.0625 | 4 | 1 | 1 | 128 |
| 7 | 0.125 | 0.0625 | 0.0125 | >16 | 0.0625 | 16 | 0.5 | 8 | 128 |
| Ketoconazole | 4 | 1 | 2 | >128 | 0.0312 | 32 | 128 | 16 | 128 |

In the guinea pig trichophytosis model (Trichophyton mentagrophytes; cf. Heffter-Heubner: Handbuch der exp. Pharmakologie, Vol. XVI/II A), the novel compounds, when applied externally, show no recurrences and are more effective than the comparison substance also tested.

The action of the test substances when used topically in the experimental Candida albicans vaginitis model was also good.

The novel compounds are also orally effective. In the model of experimental generalized candidosis of the mouse or the model of experimental Candida albicans vaginitis in the rat, complete elimination of the infections could be achieved when the test substances were administered orally in small therapeutic doses.

The novel compounds are therefore particularly useful for the treatment of fungal infections in man and animals by external application or oral administration. Examples of fields of indication in man and animals are dermatomycoses, in particular those caused by dermatophytes, such as species of the genera Epidermatophyton, Microsporum or Trichophyton, yeasts, such as species of the genera Candida, and molds, such as species of the genera Aspergillus, Mucor and Absidia.

The compounds can be used alone or together with other conventional active compounds, in particular antibiotics.

The chemotherapeutic agents or formulations are prepared in a conventional manner, in particular by mixing an appropriate dose with conventional solid, semisolid or liquid carriers or diluents and the conventional pharmaceutical auxiliaries, in accordance with the desired route of administration (cf. H. Sucker et al., Pharmazeutische Technologie, Thieme-Verlag, Stuttgart, 1978.)

Examples of suitable formulations are tablets, coated tablets, capsules, pills, aqueous solutions, suspensions and emulsions, and if appropriate sterile injectable solutions, non-aqueous emulsions, suspensions and solutions, ointments, creams, pastes, lotions, etc.

The therapeutically active compound is preferably present in the pharmaceutical formulations in a concentration of from 0.01 to 90% by weight, based on the total mixture.

To achieve the desired results in the case of oral administration either in human or in veterinary medicine, the active compound or compounds can be administered in general in amounts of from about 1.0 to about 50.0, preferably from 2 to 10, mg/kg of body weight per day, preferably in the form of several single doses. However, it may be necessary to deviate from the stated doses, and to do this as a function of the nature and severity of the disorder, the type of formulation and the route of administration of the drug, as well as the period of or interval between administrations. Thus, it may be sufficient in some cases to use less than the abovementioned amount of active compounds, while in other cases the above amount of active compound has to be exceeded.

The examples and methods which follow illustrate the preparation of the novel compounds and their intermediates.

EXAMPLE 1

(a) Preparation of the intermediates

A solution of 10.4 g of triazole in 20 ml of dry dimethylformamide was added to 2.2 g of sodium hydride (50% strength dispersion in mineral oil) in 10 ml of dry dimethylformamide at 5° C., and the mixture was stirred for 10 minutes at room temperature. 22.3 g of cis-2-bromomethyl-2-(2,4-dichlorophenyl)-4-benzoyloxymethyl-1,3-dioxolane in 100 ml of dry dimethylformamide were then added, 1 g of potassium iodide was introduced and the mixture was then stirred overnight at 145° C. The cooled reaction solution was poured into water and extracted with ethyl acetate. The extracts were evaporated down, the residue was taken up in diethyl ether, the basic components were precipitated with hydrogen chloride gas, and the supernatant solvent was decanted. The remaining precipitate was taken up in 100 ml of dioxane, 100 ml of 2 N sodium hydroxide solution were added, and the stirred mixture was refluxed for 2 hours. The reaction solution was evaporated down to half its volume in a rotary evaporator, the residue was poured into water and the mixture was extracted with methylene chloride. The extracts were washed neutral, dried over magnesium sulfate and filtered. The solvent was evaporated off and the residue was recrystallized from ethyl acetate to give 13.7 g (83%) of cis-2-(1,2,4-triazol-1-ylmethyl)-2-(2,4-dichlorophenyl)-4-hydroxymethyl-1,3-dioxolane of melting point 134°-137° C.

1.63 g of methanesulfonyl chloride were added dropwise to 3.96 g of cis-2-(1,2,4-triazol-1-ylmethyl)-2-(2,4-dichlorophenyl)-4-hydroxymethyl-1,3-dioxolane in 50 ml of dry methylene chloride and 1.44 g of triethylamine, and the reaction solution was stirred at room temperature. When the reaction was complete, the mixture was poured onto water and extracted with methylene chloride, the organic phase was washed with water, dried over magnesium sulfate and filtered, and the solvent was evaporated off. The residue was crystallized from isopropanol and gave 4.2 g (85.7%) of cis-2-(1,2,4-triazol-1-ylmethyl)-2-(2,4-dichlorophenyl)-4-methanesulfonyloxymethyl-1,3-dioxolane of melting point 95.5°-97° C.

(b) Preparation of the end product 4.2 g of cis-2-(1,2,4-triazol-1-ylmethyl)-2-(2,4-dichlorophenyl)-4-methanesulfonyloxymethyl-1,3-dioxolane were stirred with 6.6 g of sodium azide in 50 ml of dry dimethylformamide for 30 minutes at 100° C. The reaction solution was poured onto water and extracted with ethyl acetate, the extracts were washed with water, dried over magnesium sulfate and evaporated down, and the sirupy residue was taken up in acetone. When hydrogen chloride was introduced into the solution, 3.5 g (86.7%) of cis-2-(1,2,4-triazol-1-ylmethyl)-2-(2,4-dichlorophenyl)-4-azidomethyl-1,3-dioxolane were obtained in the form of the hydrochloride of melting point 164°-166° C.

EXAMPLE 2

(a) Preparation of the intermediates 268 g of α-bromo-2,4-dichloroacetophenone, 121 g of 2-hydroxymethyl-2-methylpropane-1,3-diol and 2 g of p-toluenesulfonic acid in 1000 ml of toluene were refluxed under a water separator. When the reaction was complete, the cold solution was washed neutral with sodium carbonate solution and water and dried over sodium sulfate, the solvent was evaporated off, and the oily residue was purified over an 800 g silica gel column, using a 20:1 hexane/ethyl acetate mixture. When the solvent had been evaporated off, the combined product fractions gave 255 g (69%) of 2-bromomethyl-2-(2,4-dichlorophenyl)-5-hydroxymethyl-5-methyl-1,3-dioxane as a viscous oily mixture of the two diastereomers. The mixture gradually solidified (melting range: 90°-100° C.).

21.3 g of benzoyl chloride were added to 45.8 g of this diastereomer mixture, and the resulting mixture was then stirred with 15.3 g of triethylamine in 200 ml of dry tetrahydrofuran for 2 hours at room temperature. The precipitate was filtered off, the solvent was substantially evaporated off, the residue was taken up in ethyl acetate, and the solution was washed with water, dried over sodium sulfate, filtered and evaporated down. The residue was recrystallized from ethanol to give 37 g (63.4%) of 2-bromomethyl-2-(2,4-dichlorophenyl)-5-benzoyloxymethyl-5-methyl-1,3-dioxane (isomer A) of melting point 139°-142° C.

8.5 g of this product (isomer A) and 4.9 g of imidazole were refluxed with 0.3 g of potassium iodide in 30 ml of dry dimethylformamide under nitrogen.

When the reaction was complete, the cold solution was poured onto water and extracted with ethyl acetate, the extracts were evaporated down, the residue was taken up in 50 ml of dioxane, and the stirred solution was refluxed with 10 ml of 2 N sodium hydroxide solution for 1.5 hours. The cold solution was poured onto water and extracted with methylene chloride, the extracts were dried over sodium sulfate, the solvent was evaporated off and the resulting residue was recrystallized from diethyl ether to give 4.7 g (73.5%) of 2-(imidazol-1-ylmethyl)-2-(2,4-dichlorophenyl)-5-hydroxymethyl-5-methyl-1,3-dioxane (isomer A) of melting point 174°-175° C.

(b) Preparation of the end product 1.1 g of p-toluenesulfonyl chloride were added to 1.78 g of this product (isomer A) and 0.6 g of triethylamine in 30 ml of dry methylene chloride. After 2 hours' stirring at room temperature, the mixture was poured onto water and extracted with methylene chloride, and the organic phase was washed with water, dried over magnesium sulfate, filtered and evaporated down.

The residue was taken up in 20 ml of dry dimethylformamide, 3.3 g of sodium azide were added and the mixture was stirred for 2 hours at 100° C. The cold solution was poured onto water and extracted with ethyl acetate, and the organic phase was washed with water, dried over sodium sulfate, filtered and evaporated to dryness. The residue was recrystallized from diisopropyl ether to give 1.3 g (68%) of 2-(imidazol-1-ylmethyl)-2-(2,4-dichloro-phenyl)-5-azidomethyl-5-methyl-1,3-dioxane of melting point 132° to 133° C.

The compounds listed in Table 2 were prepared, or can be prepared, by methods similar to those described in Examples 1 and 2.

TABLE 2

| Example | Z | R | R¹ | m | Salt | Mp. [°C.] |
|---|---|---|---|---|---|---|
| 3 | N | C(CH₃)₃ | CH₃ | 1 | | |
| 4 | CH | 2,4-Cl₂—C₆H₃ | C₂H₅ | 1 | | |
| 5 | N | C(CH₃)₃ | H | 0 | HCl | 172–173 |
| 6 | N | 2,4-Cl₂—C₆H₃ | n-C₃H₇ | 1 | | |
| 7 | CH | 2,4-Cl₂—C₆H₃ | H | 0 | | 85 |
| 8 | CH | 2,4-Cl₂—C₆H₃ | CH(CH₃)₂ | 1 | | |
| 9 | CH | C(CH₃)₃ | CH₃ | 1 | | |
| 10 | CH | C(CH₃)₃ | n-C₃H₇ | 1 | | |
| 11 | CH | C(CH₃)₃ | H | 0 | | |
| 12 | N | 4-Cl—C₆H₄ | CH₃ | 1 | | |
| 13 | N | 2,4-Cl₂—C₆H₃ | C₂H₅ | 1 | | |
| 14 | N | 4-F—C₆H₄ | H | 0 | | |
| 15 | CH | 4-F—C₆H₄ | H | 0 | | |

Examples of pharmaceutical formulations:

EXAMPLE A

Tablet containing 250 mg of active compound Composition for 1,000 tablets:

| | |
|---|---|
| Active compound of Example No. 7 | 250 g |
| Potato starch | 100 g |
| Lactose | 50 g |
| 4% strength gelatine solution | 45 g |
| Talc | 10 g |

Preparation:

The finely powdered active compound, potato starch and lactose are mixed. The mixture is moistened thoroughly with about 45 g of 4% strength gelatine solution and then converted to fine granules, and these are dried. The dry granules are passed through a sieve and mixed with 10 g of talc and the mixture is converted to tablets on a rotary tablet machine. The tablets are introduced into tightly closing polypropylene containers.

EXAMPLE B

Cream containing 1% of active compound

| | |
|---|---|
| Active compound of Example No. 7 | 1.0 g |
| Glycerol monostearate | 10.0 g |
| Cetyl alcohol | 4.0 g |
| Polyethylene glycol-400 stearate | 10.0 g |
| Polyethylene glycol sorbitan monostearate | 10.0 g |
| Propylene glycol | 6.0 g |
| Methyl p-hydroxybenzoate | 0.2 g |
| Demineralized water to make up to | 100.0 g |

Preparation:

The very finely powdered active compound is suspended in propylene glycol, and the suspension is stirred into a melt consisting of glycerol monostearate, cetyl alcohol, polyethylene glycol-400 stearate and polyethylene glycol sorbitan monostearate, the melt being heated at 65° C. An aqueous solution of the methyl p-hydroxybenzoate, at 70° C., is emulsified with this mixture. When it has cooled, the cream is homogenized by means of a colloid mill and is introduced into tubes.

EXAMPLE C

Powder containing 1% of active compound

| | |
|---|---|
| Active compound of Example No. 7 | 1.0 g |
| Zinc oxide | 10.0 g |
| Magnesium oxide | 10.0 g |
| Highly disperse silica | 2.5 g |
| Magnesium stearate | 1.0 g |
| Talc | 75.5 g |

Preparation:

The active compound is micronized in an air-jet mill and then mixed homogeneously with the other components. The mixture is forced through a sieve (mesh No. 7) and introduced into polyethylene containers provided with a dusting attachment.

We claim:

1. An azolylmethylcycloacetal of the formula I $$\begin{array}{c} N \nearrow \\ \Big\downarrow \\ Z \end{array} \!\! N-CH_2 \!\! \diagup\!\!\!\diagdown_{R} \!\! \diagup\!\!\!\! \begin{array}{c} O-(CH_2)_m \\ \diagdown \\ O-\!\!-CH_2 \end{array} \!\! \diagup\!\!\!\diagdown \begin{array}{c} R^1 \\ \\ CH_2-N_3 \end{array} \quad (I)$$

where R is phenyl which can be substituted by halogen, or is $C_1$–$C_6$-alkyl, $R^1$ is hydrogen or $C_1$–$C_3$-alkyl, Z is CH or N, and m is 0 or 1, and its physiologically tolerated addition salts with acids.

2. An azolylmethylcycloacetal of the formula I as claimed in claim 1, wherein R is tert.-butyl or halogen-substituted phenyl, $R^1$ is hydrogen or methyl, Z is CH or N, and m is 0 or 1, and its physiologically tolerated addition salts with acids.

3. 2-(2,4-Dichlorophenyl)-2-(1H-imidazol-1-ylmethyl)-1,3-dioxolan-4-ylmethyl azide and its physiologically tolerated addition salts with acids.

4. 2-(2,4-Dichlorophenyl)-2-(1H-imidazol-1-ylmethyl)-5-methyl-1,3-dioxolan-5-ylmethyl azide and its physiologically tolerated addition salts with acids.

5. 2-(2,4-Dichlorophenyl)-2-(1H-1,2,4-triazol-1-ylmethyl)-1,3-dioxolan-4-ylmethyl azide and its physiologically tolerated addition salts with acids.

6. A therapeutic composition comprising a pharmaceutical excipient and an effective amount of an azolylmethylcycloacetal of the formula I according to claim 1 as the active compound.

7. The method of treating mycoses in a patient suffering therefrom, which comprises administering an effective amount of an azolylmethylcycloacetal of the formula I according to claim 1.

* * * * *